US010077279B2

(12) United States Patent
Rossle et al.

(10) Patent No.: US 10,077,279 B2
(45) Date of Patent: Sep. 18, 2018

(54) VINYLSILANES FOR USE IN FUNCTIONALIZED ELASTOMERIC POLYMERS

(71) Applicant: Trinseo Europe GmbH, Horgen (CH)

(72) Inventors: Michael Rossle, Merseburg (DE); Daniel Heidenreich, Halle (DE); Christian Doring, Markranstadt (DE); Sven Thiele, Halle (DE)

(73) Assignee: TRINSEO EUROPE GMBH, Horgen (CH)

( * ) Notice: Subject to any disclaimer, the term of this patent is extended or adjusted under 35 U.S.C. 154(b) by 326 days.

(21) Appl. No.: 15/030,240

(22) PCT Filed: Oct. 18, 2013

(86) PCT No.: PCT/EP2013/071850
§ 371 (c)(1),
(2) Date: Apr. 18, 2016

(87) PCT Pub. No.: WO2015/055252
PCT Pub. Date: Apr. 23, 2015

(65) Prior Publication Data
US 2016/0264601 A1 Sep. 15, 2016

(51) Int. Cl.
| | | |
|---|---|---|
| *C07F 7/10* | (2006.01) | |
| *C07F 7/08* | (2006.01) | |
| *C07F 7/18* | (2006.01) | |
| *C08L 9/06* | (2006.01) | |
| *C08K 3/06* | (2006.01) | |
| *C08K 3/22* | (2006.01) | |
| *C08K 3/36* | (2006.01) | |
| *C08K 5/09* | (2006.01) | |
| *C08K 5/18* | (2006.01) | |
| *C08K 5/31* | (2006.01) | |
| *C08K 5/47* | (2006.01) | |
| *C08K 5/548* | (2006.01) | |
| *C08L 9/00* | (2006.01) | |
| *C08L 91/00* | (2006.01) | |
| *C08K 3/013* | (2018.01) | |
| *C08F 236/10* | (2006.01) | |

(52) U.S. Cl.
CPC .............. *C07F 7/10* (2013.01); *C07F 7/0863* (2013.01); *C07F 7/1868* (2013.01); *C08K 3/013* (2018.01); *C08K 3/06* (2013.01); *C08K 3/22* (2013.01); *C08K 3/36* (2013.01); *C08K 5/09* (2013.01); *C08K 5/18* (2013.01); *C08K 5/31* (2013.01); *C08K 5/47* (2013.01); *C08K 5/548* (2013.01); *C08L 9/00* (2013.01); *C08L 9/06* (2013.01); *C08L 91/00* (2013.01); *C08F 236/10* (2013.01)

(58) Field of Classification Search
CPC .......... C07F 7/10; C07F 7/0863; C07F 7/1868
See application file for complete search history.

(56) References Cited

U.S. PATENT DOCUMENTS

| | | |
|---|---|---|
| 3,078,254 A | 2/1963 | Zelinski |
| 3,244,664 A | 4/1966 | Zelinski |
| 3,281,383 A | 10/1966 | Zelinski |
| 3,485,857 A | 12/1969 | Speier |
| 3,692,874 A | 9/1972 | Farrar |
| 3,978,103 A | 8/1976 | Meyer-Simon |
| 4,048,206 A | 9/1977 | Voronkov |
| 4,147,711 A | 4/1979 | Bargain et al. |
| 4,474,908 A | 10/1984 | Wagner |
| 4,616,069 A | 10/1986 | Watanabe |
| 5,504,147 A * | 4/1996 | Fujiki ................ C08K 9/06 523/209 |
| 6,229,036 B1 | 5/2001 | Batz-Sohn |
| 6,777,569 B1 | 8/2004 | Westmeyer |
| 8,299,167 B2 | 10/2012 | Oshima |
| 8,318,858 B2 | 11/2012 | Oshima |
| 8,765,887 B2 * | 7/2014 | Luo .................... C08F 36/04 526/164 |
| 9,290,644 B2 | 3/2016 | Sato et al. |
| 2005/0124740 A1 | 6/2005 | Klockmann |
| 2005/0159513 A1 | 7/2005 | Henning |
| 2010/0056712 A1 | 3/2010 | Oshima |
| 2013/0131263 A1 | 5/2013 | Nebhani |
| 2013/0281645 A1 | 10/2013 | Lawson et al. |

FOREIGN PATENT DOCUMENTS

| | | |
|---|---|---|
| CN | 101659732 | 3/2010 |
| CN | 103313863 | 9/2013 |
| DE | 102009039127 A1 | 4/2010 |
| EP | 0 341 496 B1 | 11/1989 |
| JP | S506240 B1 * | 3/1975 |
| JP | 57136589 | 8/1982 |

(Continued)

OTHER PUBLICATIONS

SciFinder Scholar abstract for Asada, JPS506240 B, 1975, downloaded from SciFInder Scholar on May 9, 2018.*
Machine translation of JPS506240 B, 1975, downloaded from Espacenet on May 9, 2018.*
First Office Action for corresponding China Application No. 201380080315.5 dated Nov. 29, 2017, 10 pages including English Translation.
Office Action, and English language translation thereof, in corresponding Japanese Application No. 2016-524003, dated Aug. 9, 2017, 8 pages.
Search Report, and English language translation thereof, in corresponding Russian Federation Application No. 2016118991/04(029806), dated Dec. 11, 2017, 4 pages.

(Continued)

*Primary Examiner* — Nicholas E Hill
(74) *Attorney, Agent, or Firm* — Barnes & Thornburg LLP; G. Peter Nichols

(57) ABSTRACT

The present invention relates to novel vinylsilane compounds which are useful as modifying monomers in the polymerization of conjugated diene monomers, optionally together with aromatic vinyl monomers, thus producing polymers, specifically elastomeric polymers, which can favorably be used in rubber articles such as tires.

26 Claims, No Drawings

(56) References Cited

FOREIGN PATENT DOCUMENTS

| | | | | |
|---|---|---|---|---|
| JP | S57136589 A | * | 8/1982 | |
| JP | H10287747 A | * | 10/1998 | |
| JP | 2004-244357 A | | 9/2004 | |
| JP | 2010-270292 A | | 12/2010 | |
| JP | 2012-131890 A | | 7/2012 | |
| JP | 2012-131891 A | | 7/2012 | |
| JP | 2012-131892 A | | 7/2012 | |
| JP | 2012-131893 A | | 7/2012 | |
| JP | 2012-136658 A | | 7/2012 | |
| JP | 2012-177085 A | | 9/2012 | |
| JP | 2013-067677 A1 | | 4/2013 | |
| SG | 159474 A1 | | 3/2010 | |
| SU | 328114 | | 2/1972 | |
| SU | 612633 | | 6/1978 | |
| WO | WO 2007/047943 | | 4/2007 | |
| WO | WO 2009/148932 | | 12/2009 | |
| WO | WO 2011/028523 | | 3/2011 | |
| WO | WO 2012/091753 | | 7/2012 | |
| WO | WO 2012/144488 | | 10/2012 | |
| WO | WO 2013/077018 A1 | | 5/2013 | |
| WO | WO 2014/040639 | | 3/2014 | |
| WO | WO 2014/040640 | | 3/2014 | |
| WO | WO 2015/010710 | | 1/2015 | |

OTHER PUBLICATIONS

Written Opinion and International Search Report dated Jul. 1, 2014 out of corresponding priority Application No. PCT/EP2013/071850 (7 pages).

International Preliminary Report on Patentability dated Apr. 19, 2016 out of corresponding priority Application No. PCT/EP2013/071850 (4 pages).

Corrected Written Opinion and International Search Report dated Jun. 7, 2016 out of corresponding priority Application No. PCT/EP2013/071850 (3 pages).

* cited by examiner

VINYLSILANES FOR USE IN FUNCTIONALIZED ELASTOMERIC POLYMERS

This application claims priority to PCT/EP2013/071850 filed Oct. 18, 2013, the entire contents of which is incorporated herein by reference.

FIELD OF THE INVENTION

The present invention is directed to novel vinylsilane compounds which are useful as modifying monomers in the polymerization of conjugated diene monomers, optionally together with aromatic vinyl monomers, thus producing polymers, specifically elastomeric polymers, which can favorably be used in rubber articles such as tires.

BACKGROUND OF THE INVENTION

Increasing oil prices and national legislation requiring the reduction of automotive carbon dioxide emissions force tire and rubber producers to produce "fuel-efficient" and thus fuel-saving tires. One approach for obtaining fuel-efficient tires lies in the production of tire formulations having reduced hysteresis loss. The hysteresis loss of a cross-linked elastomeric polymer composition is related to its tan δ value at 60° C. (see ISO 4664-1:2005; Rubber, Vulcanized or thermoplastic; Determination of dynamic properties—part 1: General guidance). In general, vulcanized elastomeric polymer compositions having relatively low tan δ values at 60° C. are preferred as having lower hysteresis loss. In the final tire product, this translates into a lower rolling resistance and better fuel economy. In contrast, a lower tan δ value at 0° C. corresponds to a deteriorated wet grip of the tire product. Thus, it is generally accepted that a lower rolling resistance tire can be made at the expense of deteriorated wet grip properties. For example, if, in a random solution styrene-butadiene rubber (random SSBR), the polystyrene unit concentration is reduced with respect to the total polybutadiene unit concentration, the SSBR glass transition temperature is reduced and, as a result, both tan δ at 60° C. and tan δ at 0° C. are reduced, generally corresponding to improved rolling resistance and deteriorated wet grip performance of the tire. Accordingly, when assessing the rubber vulcanizate performance correctly, both tan δ at 60° C. and tan δ at 0° C. should be monitored along with the tire heat build-up.

WO 2012/091753 relates to silane-functionalized polymers and rubber vulcanizates prepared therefrom. The authors describe the use of certain alkenylaminosilanes for use in the initiation of anionic polymerizations.

US 2010/0056712 relates to a conjugated diene polymer obtained by polymerizing a conjugated diene monomer and a vinylaminosilane in the presence of an alkali metal catalyst.

WO 2011/028523 relates to a process for preparing a polydiene, the process comprising the polymerization of a conjugated diene monomer with a lanthanide-based catalyst system in the presence of a vinylsilane, an allylsilane, or an allylvinylsilane.

The present invention aims the provision of cured elastomeric polymer (rubber) compositions exhibiting reduced heat build-up and improved tan δ values, corresponding to an improved balance of rolling resistance and wet grip performance.

SUMMARY OF THE INVENTION

The present invention is inter alia based on the finding that the above objects can be solved by carrying out the polymerization of conjugated diene monomers such as 1,3-butadiene ("butadiene") and isoprene in the presence of a specific vinylsilane compound.

Thus, in a first aspect, the present invention provides a vinylsilane compound of the following Formula 1:

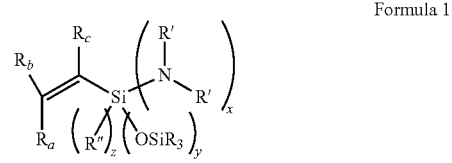

Formula 1 wherein R is independently selected from $C_1$-$C_{18}$ hydrocarbyl;
R" is selected from $C_1$-$C_6$ hydrocarbyl;
$R_a$, $R_b$ and $R_c$ are independently selected from hydrogen, methyl, ethyl and vinyl;
x and y are independently integers selected from 1 and 2;
z is an integer selected from 0 and 1; and x+y+z=3;
R' is independently selected from $C_1$-$C_{12}$ alkyl, $C_2$-$C_{12}$ alkenyl, $C_6$-$C_{18}$ aryl, $C_7$-$C_{18}$ alkylaryl, and tri($C_1$-$C_6$ alkyl, $C_6$-$C_{12}$ aryl or $C_7$-$C_{18}$ alkylaryl)silyl, wherein the two R' groups may be connected to form a ring and the ring may contain, further to the Si-bonded nitrogen atom, one or more of an oxygen atom, a nitrogen atom, an >N($C_1$-$C_6$ alkyl) group and a sulfur atom; and one R' may be —Si($CR_c$=$CR_aR_b$)($OSiR_3$)$_y$($R''$)$_z$, wherein $R_a$, $R_b$, $R_c$, R, R", y and z are independently as defined above and y+z=2.

The vinylsilane compounds of Formula 1 include (encompass) vinylsilane compounds of the following Formulas 1' and 6:

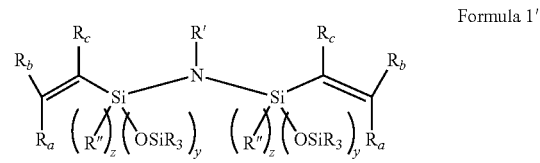

Formula 1'

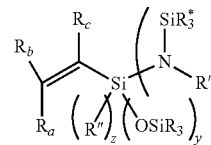

Formula 6 wherein the substituents and parameters are defined as indicated above.

In a second aspect, the present invention provides a process for preparing the vinylsilane compound of Formula 1, said process comprising reacting a dihalovinylsilane or trihalovinylsilane of Formula 2 with a tri($C_1$-$C_{18}$ hydrocarbyl)silanol of Formula 3 and a secondary aliphatic or aromatic amine of Formula 4 according to the following reaction scheme, in the presence of a proton scavenger such as a tertiary aliphatic or aromatic amine, a metal hydride, or an organometal compound. In one embodiment, the vinylsilane compound of Formula 1 is represented by Formula 6, as shown below, and is prepared in a process comprising reacting a dihalovinylsilane or trihalovinylsilane of Formula 2 with a tri($C_1$-$C_{18}$ hydrocarbyl)silanol of Formula 3, a primary aliphatic or aromatic amine of Formula 4' and a halosilane of Formula 5 in the presence of a proton scavenger such as a tertiary aliphatic or aromatic amine, a metal hydride, or an organometal compound. In an embodiment, it is also possible to use the primary amine of Formula 4' or the secondary amine of Formula 4 as the proton scavenger, which however requires using a higher amount of such amine.

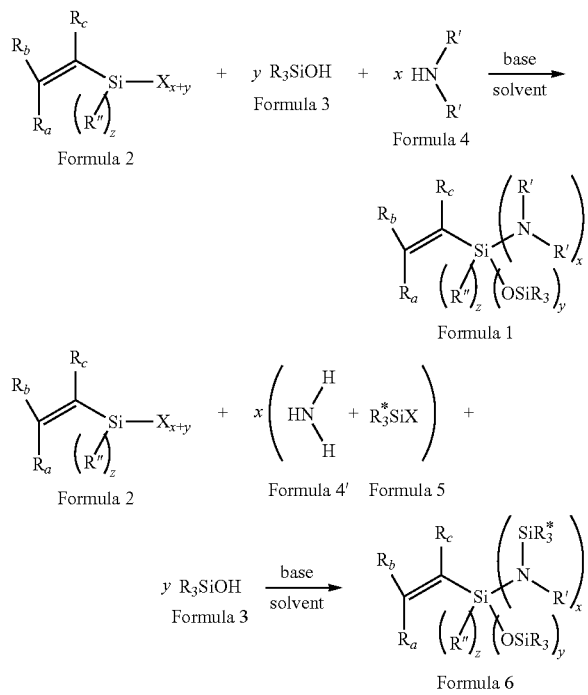

wherein R, R", $R_a$, $R_b$, $R_c$, x, y and z are as defined for Formula 1, R* is independently selected from $C_1$-$C_6$ alkyl, $C_6$-$C_{12}$ aryl and $C_7$-$C_{18}$ alkylaryl, and X is a halogen such as chlorine or bromine, preferably chlorine.

In a third aspect, the present invention provides a process for preparing an elastomeric polymer, said process comprising polymerizing at least one conjugated diene monomer, a vinylsilane compound of Formula 1, including a vinylsilane compound of Formula 6, and optionally one or more aromatic vinyl monomers in the presence of an initiator compound or a catalyst, preferably in the presence of an initiator compound.

In a fourth aspect, the present invention provides an elastomeric polymer obtainable by polymerizing at least one conjugated diene monomer, a vinylsilane compound of Formula 1, including a vinylsilane compound of Formula 6, and optionally one or more aromatic vinyl monomers in the presence of an initiator compound or a catalyst, preferably in the presence of an initiator compound.

In a fifth aspect, the present invention provides a non-cured polymer composition comprising the elastomeric polymer of the invention and one or more further components selected from (i) components which are added to or formed as a result of the polymerization process used for making said polymer, (ii) components which remain after solvent removal from the polymerization process, and (iii) components which are added to the polymer after completion of the polymer manufacturing process, thus including components which are added to the "solvent-free" polymer by application of (but not limited to) a mechanical mixer.

In a sixth aspect, the present invention provides a vulcanized polymer composition which is obtained by vulcanizing a non-cured polymer composition of the invention comprising one or more vulcanizing agents.

In a seventh aspect, the present invention an article comprising at least one component formed from the vulcanized polymer composition of the invention.

The elastomeric polymer and compositions thereof have beneficial properties especially when used in the manufacture of tires. Specifically, it was surprisingly found that cured polymer compositions ("cured rubber compounds") produced from the elastomeric polymer of the invention exhibit an improved balance of tan δ at 0° C. and tan δ at 60° C., reflecting a better balance of low rolling resistance and high wet grip. The beneficial properties were in particular found when using a non-cured polymer composition of the invention containing silica and/or carbon black as fillers.

DETAILED DESCRIPTION

Vinylsilane Compound of Formula 1

The vinylsilane compound of Formula 1 of the first aspect of the present invention, including the vinylsilane compound of Formulas 1' and 6, is characterized by having in combination both an amino group and a siloxy group attached to the silicon atom of the vinylsilane moiety.

In the vinylsilane compound of Formula 1 (including Formulas 1' and 6), R is independently selected from $C_1$-$C_{18}$ hydrocarbyl. $C_1$-$C_{18}$ hydrocarbyl specifically includes $C_1$-$C_{18}$ alkyl, $C_2$-$C_{18}$ alkenyl, $C_2$-$C_{18}$ alkynyl, $C_6$-$C_{18}$ aryl and $C_7$-$C_{18}$ alkylaryl. Specific exemplary trihydrocarbylsiloxy groups formed by the combination of R and the siloxy (—O—Si) group are tert-butyldimethylsiloxy, triethylsiloxy, triisopropylsiloxy, triphenylsiloxy, tert-butyldiphenylsiloxy, diethylisopropylsiloxy, dimethyloctadecylsiloxy and trihexylsiloxy.

R' is independently selected from $C_1$-$C_{12}$ alkyl, $C_2$-$C_{12}$ alkenyl, $C_6$-$C_{18}$ aryl, $C_7$-$C_{18}$ alkylaryl and tri($C_1$-$C_6$ alkyl, $C_6$-$C_{12}$ aryl or $C_7$-$C_{18}$ alkylaryl)silyl, wherein the two R' groups may be connected to form a ring and the ring may contain, further to the Si-bonded nitrogen atom, one or more of an oxygen atom, a nitrogen atom, an >N($C_1$-$C_6$ alkyl) group and a sulfur atom. R' is preferably independently selected from methyl, ethyl, n-propyl, n-butyl, isobutyl, pentyl, hexyl and benzyl. In one embodiment, the two R' groups are each an ethyl group, which are again connected via an oxygen atom, thus forming a morpholine ring with the Si-bonded nitrogen atom. In another embodiment, the two R' groups are connected to form, together with the Si-bonded nitrogen atom, a 5- to 12-membered ring, such as a cyclohexylamine group, a cycloheptylamino group, a cyclooctylamino group, a cyclododecylamino group or a cyclopentylamino group, preferably a 5- to 8-membered ring. In one embodiment, one R' represents a group —Si($CR_c$=$CR_aR_b$)$(OSiR_3)_y(R'')_z$, wherein $R_a$, $R_b$, $R_c$, R, R", y and z are independently as defined above and y+z=2. In this embodiment, the vinylsilane compound of the present invention takes the structure of Formula 1'.

R" is selected from $C_1$-$C_6$ hydrocarbyl, including $C_1$-$C_6$ alkyl and phenyl. It is preferably methyl.

$R_a$, $R_b$ and $R_c$ are independently selected from hydrogen, methyl, ethyl and vinyl. They are preferably identical and are even more preferably hydrogen. In one embodiment, only one of $R_a$, $R_b$ and $R_c$ is vinyl, while the remaining two are hydrogen.

x and y are independently integers selected from 1 and 2; z is an integer selected from 0 and 1; and x+y+z=3. In a preferred embodiment, x, y and z are each 1.

In preferred embodiments of the vinylsilane compound of Formula 1, the parameters and substituents take the following values:

a) R is (methyl, methyl, t-butyl) or (phenyl, phenyl, phenyl) or (t-butyl, phenyl, phenyl) or (hexyl, hexyl, hexyl); R' is independently selected from methyl, ethyl, n-propyl, n-butyl, pentyl, hexyl, heptyl, octyl and benzyl (bonded via methyl group), or —NR'R' forms a morpholine group, pyrrolidine group, piperidine group or oxazolidine group; R" is methyl; $R_a$, $R_b$ and $R_c$ are each hydrogen; and x=y=z=1 b) R is (methyl, methyl, t-butyl) or (hexyl, hexyl, hexyl); R' is independently selected from methyl and ethyl, or —NR'R' forms a morpholine group, pyrrolidine group, piperidine group or oxazolidine group; R" is methyl; $R_a$, $R_b$ and $R_c$ are each hydrogen; and x=2, y=1 and z=0 c) R is (methyl, methyl, t-butyl) or (hexyl, hexyl, hexyl); R' is independently selected from methyl and ethyl, or —NR'R' forms a morpholine group, pyrrolidine group, piperidine group or oxazolidine group; R" is methyl; $R_a$ and $R_b$ are each hydrogen and $R_c$ is vinyl; and x=y=z=1

Generally, it is preferred to select bulkier substituents for group —OSiR$_3$ the smaller the substituents in group —NR'$_2$ are.

In preferred embodiments of the vinylsilane compound of Formula 6, the parameters and substituents take the following values: R is (methyl, methyl, t-butyl); R' is selected from methyl, ethyl, n-propyl, n-butyl, pentyl, hexyl, heptyl and octyl; R* is selected from methyl and ethyl; R" is methyl; $R_a$, $R_b$ and $R_c$ are each hydrogen; and x=y=z=1.

Preferred embodiments of the vinylsilane compound of Formula 1 are (tert-butyldimethylsiloxy)methyl-4-morpholino(vinyl)silane, (tert-butyldimethylsiloxy)(dimethylamino)methyl(vinyl)silane, (tert-butyldimethylsiloxy)(diethylamino)methyl(vinyl)silane and (tert-butyldimethylsiloxy)(dibutylamino)methyl(vinyl)silane. Preferred embodiments of the vinylsilane compound of Formula 6 are (tert-butyldimethylsiloxy)[trimethylsilyl)propylamino]methyl(vinyl)silane(tert-butyldimethylsiloxy)[(trimethylsilypmethylamino]methyl(vinyesilane, (tert-butyldimethylsiloxy)[(trimethylsilyl)ethylamino]methyl (vinyl)silane, (tert-butyldimethylsiloxy)[(trimethylsilyl) butylamino]methyl(vinyl)silane, (tert-butyldimethylsiloxy) [(dimethylphenylsilyl)propylamino]methyl(vinyl)silane, (tert-butyldimethylsiloxy)[(dimethylphenylsilyl)ethylamino]methyl(vinyl)silane and (tert-butyldimethylsiloxy) [(dimethylphenylsilyl)methylamino]methyl(vinyl)silane.

Preparation of Vinylsilane Compound of Formula 1 (including Formulas 1' and 6)

According to the second aspect of the invention, the vinylsilane compound of Formula 1 can be prepared by reacting a dihalovinylsilane or trihalovinylsilane of Formula 2 with a tri($C_1$-$C_{18}$ hydrocarbyl)silanol of Formula 3 and a secondary aliphatic or aromatic amine of Formula 4, wherein R, R', R", $R_a$, $R_b$, $R_c$, x, y and z are as defined for Formula 1, generally and in specific embodiments. The vinylsilane compound of Formula 6, as encompassed by Formula 1, can be prepared in a corresponding manner, yet using a combination of a primary aliphatic or aromatic amine of Formula 4' and a halosilane of Formula 5 instead of the secondary amine of Formula 4.

Useful dihalovinylsilanes of Formula 2 include dichlorovinylsilane. Useful trihalovinylsilanes of Formula 2 include trichlorovinylsilane.

The tri($C_1$-$C_{18}$ hydrocarbyl)silanol of Formula 3 is specifically exemplified by tert-butyldimethylsilanol, triethylsilanol, triisopropylsilanol, trimethylsilanol, triphenylsilanol, tert-butyldiphenylsilanol, diethylisopropylsilanol, dimethylphenylsilanol, benzyldimethylsilanol and dimethyloctadecylsilanol. The silanol of Formula 3 is generally used in a total amount of 0.9 to 5 equivalents per equivalent of the halovinylsilane of Formula 2. In case of x=y=z=1 in Formula 1 or 6, it is preferred to use the silanol of Formula 3 in a total amount of 0.9-2 equivalents, more preferably 0.9-1.4 equivalents, per equivalent of the halovinylsilane of Formula 2. In case of x=1, y=2 and z=0, it is preferred to use the silanol of Formula 3 in a total amount of 1.9-5 equivalents, more preferably 1.9-3 equivalents, per equivalent of the halovinylsilane of Formula 2. In case of x=2, y=1 and z=0, it is preferred to use the silanol of Formula 3 in a total amount of 0.9-2 equivalents, more preferably 0.9-1.4 equivalents, per equivalent of the halovinylsilane of Formula 2.

Useful secondary aliphatic or aromatic amines of Formula 4 and primary aliphatic or aromatic amines of Formula 4' include dimethylamine, diethylamine, dipropylamine, diisopropylamine, dibutylamine, diisobutylamine, dipentylamine, dihexylamine, diheptylamine, dioctylamine, dinonylamine, didecylamine, diisooctylamine, N-benzylmethylamine, N-methylaniline, N-ethylaniline, morpholine, pyrrolidine, piperidine, N-methylpiperazine, methylamine, ethylamine, propylamine, butylamine, pentylamine, hexylamine, heptylamine and octylamine, preferably dimethylamine, diethylamine, dibutylamine, morpholine and propylamine. The amine of Formula 4 or 4' is generally used in a total amount of 0.9 to 5 equivalents per equivalent of the halovinylsilane of Formula 2. In case of x=y=z=1 in Formula 1 or 6, it is preferred to use the amine of Formula 4 or 4' in a total amount of 0.9-2 equivalents, more preferably 0.9-1.4 equivalents, per equivalent of the halovinylsilane of Formula 2. In case of x=1, y=2 and z=0, it is preferred to use the amine of Formula 4 or 4' in a total amount of 0.9-2 equivalents, more preferably 0.9-1.4 equivalents, per equivalent of the halovinylsilane of Formula 2. In case of x=2, y=1 and z=0, it is preferred to use the amine of Formula 4 or 4' in a total amount of 1.8-5 equivalents, more preferably 1.9-3 equivalents, per equivalent of the halovinylsilane of Formula 2.

Useful halosilanes of Formula 5 for preparing a vinylsilane compound of Formula 6 include trimethylchlorosilane, triethylchlorosilane, dimethylbenzylchlorosilane and dimethylphenylchlorosilane. The halosilane of Formula 5 is generally used in a total amount of 1-2 equivalents per equivalent of the primary amine of Formula 4'.

For capturing and neutralizing the hydrohalic acid formed in the course of the reaction, a proton scavenger is generally used, including tertiary aliphatic or aromatic amines, metal hydrides and organometal compounds. Specific embodiments of the proton scavenger include sodium hydride, lithium hydride, potassium hydride, calcium hydride, n-butyllithium, triethylamine and pyridine, preferably triethylamine, lithium hydride and sodium hydride. It is also possible to use the amine of Formula 4 or 4' as a proton scavenger, yet it will then be necessary to increase its amount by 1.5-5 equivalents. The proton scavenger is generally used in a total amount of 1.5 to 5 equivalents, preferably 2 to 4 equivalents, per equivalent of the halovinylsilane of Formula 2.

The reaction can be carried out in a solvent, especially in an inert solvent, such as a hydrocarbon solvent, including pentane, n-hexane, cyclohexane, heptane, benzene and toluene, an ether solvent, including diethylether, tetrahydrofuran and tert-butylmethylether, a chlorinated solvent, including chloroform, tetrachloromethane and dichloromethane, an ester solvent such as ethyl acetate and methyl acetate, or other dipolar solvents like acetone, dimethylformamide and acetonitrile. Preferred solvents are dichloromethane, diethylether, ethyl acetate, toluene and cyclohexane. The total concentration of the reactants in the solvent is usually in the range of from 0.1 to 1 M.

The reaction can suitably be carried out at a temperature of from −30° C. to the reflux temperature of the reaction mixture, preferably from 0° C.-25° C.

Usually, the reaction is carried out by dropwise adding the silanol of Formula 3, in solution or neat, to a solution of the halovinylsilane of Formula 2 and the proton scavenger. The reaction mixture is stirred and reacted for a sufficient time, generally for several hours and preferably for at least one hour, at a temperature of usually 0-50° C. Subsequently, the amine of Formula 4 or 4' is added to the reaction mixture, and the reaction mixture is stirred and reacted for a sufficient time, generally for several hours, at a temperature of 0° C. to the reflux temperature of the reaction mixture. In the case of preparing a vinylsilane compound of Formula 6 using a primary amine of Formula 4', the halosilane of Formula 5 is then added, and the reaction mixture is stirred and reacted for a sufficient time, generally for several hours at a temperature of 25° C.-50° C. After termination or completion of the reaction, insoluble salts formed in the course of the reaction can be filtered off, the solvent can be removed by distillation under reduced pressure, and purification such as via vacuum distillation or recrystallization provides the vinylsilane of Formula 1 (including Formula 6).

Polymerization

The process for preparing the elastomeric polymer according to the third aspect of the present invention comprises polymerizing at least one conjugated diene monomer, a vinylsilane compound of Formula 1 and optionally one or more aromatic vinyl monomers in the presence of an initiator compound. The elastomeric polymer can be prepared generally via anionic, radical or transition metal-catalyzed polymerization, but is preferably prepared by anionic polymerization. Two or more vinylsilane compounds of Formula 1 may be used in combination. The polymerization may be conducted in a solvent and may be carried out with one or more of chain end-modifying agents, coupling agents incl. modified coupling agents, randomizer compounds and polymerization accelerator compounds.

Further to the following specific disclosure, generally applicable directions on polymerization technologies including polymerization initiator compounds, polar coordinator compounds and accelerators (for increasing/changing the reactivity of the initiator, for randomly arranging aromatic vinyl monomers and/or for randomly arranging and/or changing the concentration of 1,2-polybutadiene or 1,2-polyisoprene or 3,4-polyisoprene units introduced in the polymer); the amounts of each compound; monomer(s); and suitable process conditions are described in WO 2009/148932, fully incorporated herein by reference.

Conjugated Diene Monomers

Exemplary conjugated diene monomers useful in the present invention include 1,3-butadiene, 2-($C_1$-$C_5$ alkyl)-1,3-butadiene such as isoprene (2-methyl-1,3-butadiene), 2,3-dimethyl-1,3-butadiene, 1,3-pentadiene, 2,4-hexadiene, 1,3-hexadiene, 1,3-heptadiene, 1,3-octadiene, 2-methyl-2,4-pentadiene, cyclopentadiene, 2,4-hexadiene and 1,3-cyclooctadiene. A mixture of two or more conjugated dienes may be used. Preferred conjugated dienes include 1,3-butadiene and isoprene. In one embodiment, the conjugated diene is 1,3-butadiene.

Initiator Compounds

An initiator compound is used in the polymerization process of the present invention, and two or more initiator compounds may be used in combination. The initiator compound may be a monovalent or multivalent (divalent, trivalent, etc.) initiator compound. Suitable initiator compounds include alkali metals, organoalkali metal compounds, a complex between an alkali metal and a polar compound, an oligomer containing an alkali metal, and Lewis acid-base complexes. Exemplary alkali metals include lithium, sodium, potassium, rubidium and cesium.

Exemplary organoalkali metal compounds include ethyllithium, n-butyllithium, s-butyllithium, t-octyllithium, isopropyllithium, phenyllithium, cyclohexyllithium, 2-butyllithium, 4-phenylbutyllithium, t-butyldimethylsilyloxypropyllithium, dialkylaminopropyllithium, N-morpholinopropyllithium, lithiumdiisopropylamide, lithium piperidide, lithium pyrrolidide, dilithiated diphenylethylene compounds, multi-lithiated trivinyl benzene compounds, sodium biphenylide, sodium naphthalenide and potassium naphthalenide. Exemplary complexes between an alkali metal and a polar compound include a lithium-tetramethylethylenediamine complex, a lithium-tetrahydrofuran complex, a lithium-ditetrahydrofuranepropane complex, and the sodium and potassium analogues thereof. More preferably, the initiator compound is a mono- or dilithium alkyl, alkylaryl or aryl compound. Further useful initiators include the amino silane polymerization initiators described in PCT/EP2012/068121 and the polymerization initiators described in PCT/EP2013/065399. The total amount of the initiator(s), in particular the organolithium initiator(s), will be adjusted depending on the monomer and target molecular weight. The total amount is typically from 0.05 to 5 mmol, preferably from 0.2 to 3 mmol per 100 grams of monomer.

Aromatic Vinyl Monomers

The optional aromatic vinyl monomers include monovinylaromatic compounds, i.e. compounds having only one vinyl group attached to an aromatic group, and di- or higher vinylaromatic compounds which have two or more vinyl groups attached to an aromatic group. Exemplary aromatic vinyl monomers optionally used together with the at least one conjugated diene include styrene, $C_{1-4}$ alkyl-substituted styrene such as 2-methylstyrene, 3-methylstyrene, 4-methylstyrene, 2,4-dimethylstyrene, 2,4,6-trimethylstyrene, α-methylstyrene, 2,4-diisopropylstyrene and 4-tert-butylstyrene, stilbene, vinyl benzyl dimethylamine, (4-vinylbenzyl) dimethyl aminoethyl ether, N,N-dimethylaminoethyl styrene, tert-butoxystyrene, vinylpyridine and divinylaromatic compounds such as 1,2-divinylbenzene, 1,3-divinylbenzene and 1,4-divinylbenzene. Two or more aromatic vinyl monomers may be used in combination. A preferred aromatic vinyl monomer is a monovinylaromatic compound, more preferably styrene. The monovinylaromatic compound(s) may be used, depending on the application, in total amounts of 40-70 wt. %, or 15-40 wt. %, or 2-15 wt. %, based on the total weight of monomers used in the polymerization reaction. The di- or higher vinylaromatic compounds such as divinylbenzene, including 1,2-divinylbenzene, 1,3-divinylbenzene and 1,4-divinylbenzene, may be used in total amount of 1 wt. % or less (based on the total molar weight of the monomers used to make the polymer). In one preferred embodiment, 1,2-divinylbenzene is used in combination with styrene and butadiene or isoprene.

Other Monomers

Comonomers other than the vinylsilane of Formula 1, the conjugated diene monomer and the aromatic vinyl monomer, which may be used in preparing the elastomeric polymer of the invention, include acrylic monomers such as acrylonitrile, acrylates, e.g., acrylic acid, methyl acrylate, ethyl acrylate, propyl acrylate and butyl acrylate, and methacrylates, e.g., methyl methacrylate, ethyl methacrylate, propyl methacrylate and butyl methacrylate.

Solvent

The polymerization is usually conducted as a solution polymerization, wherein the formed polymer is substantially soluble in the reaction mixture, or as a suspension/slurry polymerization, wherein the formed polymer is substantially insoluble in the reaction medium. More preferably, the polymer is obtained in a solution polymerization. As the polymerization solvent, a hydrocarbon solvent is conventionally used which does not deactivate the initiator, catalyst or active polymer chain. The polymerization solvent may be a combination of two or more solvents. Exemplary hydrocarbon solvents include aliphatic and aromatic solvents. Specific examples include (including all conceivable constitutional isomers): propane, butane, pentane, hexane, heptane, butene, propene, pentene, hexane, octane, benzene, toluene, ethylbenzene and xylene.

Chain End-Modifying Agents

One or more chain end-modifying agents may be used in the polymerization reaction of the present invention for further controlling polymer properties by reacting with the terminal ends of the polymer chains in the polymer of the invention. Generally, silane-sulfide omega chain end-modifying agents such as disclosed in WO 2007/047943, WO 2009/148932, U.S. Pat. No. 6,229,036 and US 2013/0131263, each incorporated herein by reference in its entirety, can be used for this purpose. Other chain end-modifying agents suitable for use in the present invention are those disclosed in PCT/EP2012/068121 and PCT/EP2013/065399 and the silane sulfide modifiers described in PCT/EP2012/068120.

The chain end-modifying agents may be added intermittently (at regular or irregular intervals) or continuously during the polymerization, but are preferably added at a conversion rate of the polymerization of more than 80 percent and more preferably at a conversion rate of more than 90 percent. Preferably, a substantial amount of the polymer chain ends is not terminated prior to the reaction with the chain end-modifying agent; that is, living polymer chain ends are present and are capable of reacting with the modifying agent.

Coupling Agents

For further controlling polymer molecular weight and polymer properties, a coupling agent ("linking agent") can be used as an optional component in the process of the invention. A coupling agent will reduce hysteresis loss by reducing the number of free chain ends of the elastomeric polymer and/or reduce the polymer solution viscosity, compared with non-coupled essentially linear polymer macromolecules of identical molecular weight. Coupling agents such as tin tetrachloride may functionalize the polymer chain end and react with components of an elastomeric composition, for example with a filler or with unsaturated portions of a polymer. Exemplary coupling agents are described in U.S. Pat. No. 3,281,383, U.S. Pat. No. 3,244,664 and U.S. Pat. No. 3,692,874 (e.g., tetrachlorosilane); U.S. Pat. No. 3,978,103, U.S. Pat. Nos. 4,048,206, 4,474,908 and U.S. Pat. No. 6,777,569 (blocked mercaptosilanes); U.S. Pat. No. 3,078,254 (multi-halogen-substituted hydrocarbon, such as 1,3,5-tri(bromo methyl) benzene); U.S. Pat. No. 4,616,069 (tin compound and organic amino or amine compound); and U.S. 2005/0124740. Generally, the chain end-modifying agent is added before, during or after the addition of the coupling agent, and the modification reaction is preferably carried out after the addition of the coupling agent. The total amount of coupling agents used will influence the Mooney viscosity of the coupled polymer and is typically in the range of from 0.001 to 4.5 milliequivalents per 100 grams of the elastomeric polymer, for example 0.01 to about 1.5 milliequivalents per 100 grams of polymer.

Randomizer Compounds

Randomizer compounds as conventionally known in the art (also known as polar coordinator compounds) may optionally be added to the monomer mixture or polymerization reaction, in order to adjust the microstructure (i.e. the content of vinyl bonds) of the conjugated diene part of the polymer, or to adjust the composition distribution of any aromatic vinyl monomer and of the vinyl bonds in the polymer chain. A combination of two or more randomizer compounds may be used. Randomizer compounds useful in the invention are generally exemplified by Lewis base compounds. Suitable Lewis bases for use in the present invention are, for example, ether compounds such as diethyl ether, di-n-butyl ether, ethylene glycol diethyl ether, ethylene glycol dibutyl ether, diethylene glycol dimethyl ether, propylene glycol dimethyl ether, propylene glycol diethyl ether, propylene glycol dibutyl ether, ($C_1$-$C_8$ alkyl)tetrahydrofurylethers (including methyltetrahydrofurylether, ethyltetrahydrofurylether, propyltetrahydrofurylether, butyltetrahydrofurylether, hexyltetrahydrofurylether and octyltetrahydrofurylether), tetrahydrofuran, 2,2-(bistetrahydrofurfuryl)propane, bistetrahydrofurfurylformal, methyl ether of tetrahydrofurfuryl alcohol, ethyl ether of tetrahydrofurfuryl alcohol, butyl ether of tetrahydrofurfuryl alcohol, α-methoxytetrahydrofuran, dimethoxybenzene and dimethoxyethane, and tertiary amines such as triethylamine, pyridine, N,N,N',N'-tetramethyl ethylenediamine, dipiperidinoethane, methyl ether of N,N-diethylethanolamine, ethyl ether of N,N-diethylethanolamine, N,N-diethylethanolamine and dimethyl N,N-tetrahydrofurfuryl amine. Examples of preferred randomizer compounds are identified in WO 2009/148932, incorporated herein by reference in its entirety. The randomizer compound will typically be added at a molar ratio of randomizer compound to initiator compound of from 0.012:1 to 10:1, preferably from 0.1:1 to 8:1 and more preferably from 0.25:1 to about 6:1.

Accelerator Compounds

The polymerization can optionally include accelerators to increase the reactivity of the initiator (and, thus, to increase the polymerization rate), to randomly arrange aromatic vinyl monomers introduced into the polymer, or to provide a single chain of aromatic vinyl monomers, thus influencing the distribution of aromatic vinyl monomers in a living anionic elastomeric copolymer. Examples of accelerators include sodium alkoxides or sodium phenoxides and potassium alkoxides or potassium phenoxides, preferably potassium alkoxides or potassium phenoxides, such as potassium isopropoxide, potassium t-butoxide, potassium t-amyloxide, potassium n-heptyloxide, potassium benzyloxide, potassium phenoxide; potassium salts of carboxylic acids, such as isovaleric acid, caprylic acid, lauric acid, palmitic acid, stearic acid, oleic acid, linolenic acid, benzoic acid, phthalic acid and 2-ethyl hexanoic acid; potassium salts of organic sulfonic acids, such as dodecyl benzenesulfonic acid, tetradecyl benzenesulfonic acid, hexadecyl benzenesulfonic acid and octadecyl benzenesulfonic acid; and potassium salts of organic phosphorous acids, such as diethyl phosphite, diisopropyl phosphite, diphenyl phosphite, dibutyl phosphite, and dilauryl phosphite. Such accelerator compounds may be added in a total amount of from 0.005 to 0.5 mol per 1.0 gram atom equivalent of lithium initiator. If less than 0.005 mol is added, a sufficient effect is not typically achieved. On the other hand, if the amount of the accelerator compound is more than about 0.5 mol, the productivity and efficiency of the chain end modification reaction can be significantly reduced.

Dosing

The vinylsilane of Formula 1 can be used in an amount of from 1 equivalent per equivalent of initiator compound(s) to 50 wt. % based on the total amount of the resulting elastomeric polymer. When the polymer of the invention is used in tire applications, for example in rubber compound for a tire tread or tire sidewall, it is preferable to use the vinylsilane for Formula 1 in an amount of from 1 equivalent per equivalent of initiator compound(s) to 20 wt. %, more preferably up to 10 wt. %, even more preferably up to 5 wt. % based on the elastomeric polymer. The remaining amount of the elastomeric polymer is derived from the conjugated diene monomer and optional aromatic vinyl monomer as well as further optional components, such as chain end-modifying agents, coupling agents and randomizers.

The mode of addition ("dosing") of the vinylsilane of Formula 1 in the polymerization process relative to the conjugated diene monomer and optional aromatic vinyl monomer, initiator compound and other components will affect the structure of the resulting polymer. Thus, statistical copolymers and block copolymers having blocks of vinylsilane polymer and blocks of other monomers in desired proportions and sequences can be prepared. For example, the following polymer structures could be envisaged for adjusting polymer properties (without intending any limitation on dosing options generally available):

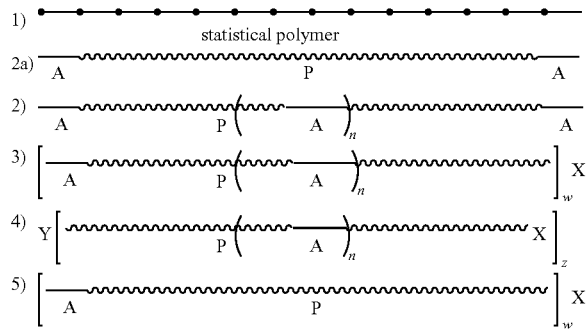

A: block of polymer of vinylsilane compound of Formula 1 or tapered structure element or single monomer unit P: polymer of conjugated diene monomer, optionally with other monomers (except for vinylsilane compound of Formula 1)

X: polar group obtained by reacting living polymer chain with polar molecule

Y: mono- or diinitiator incorporated into polymer chain w: 1, 2, 3 or 4 z: 1, 2 or 3 (z represents the number of polymer arms as result of the coupling process when using coupling agents)

The above polymer structures can be obtained in the following fashion:

(1) Continuous (incremental) addition of the vinylsilane compound of Formula 1 to a mixture comprising conjugated diene monomer, optionally aromatic vinyl monomer, and initiator compound, as the polymerization proceeds, results in the provision of a statistical copolymer.

(2a) Dosing of vinylsilane compound of Formula 1 before addition of main amount of initiator a) together with main amounts of comonomers (tapered structure) or b) without other comonomers, which can be added after conversion of vinylsilane to generate block structure. After quantitative or close to quantitative conversion of monomers, a second addition of vinylsilane can be performed to generate block structure at polymer end. If A is a single monomer unit, the resulting structure is an alpha-omega-modified polymer.

(2), (3) Dosing of vinylsilane compound of Formula 1 before addition of main amount of initiator a) together with main amounts of comonomers (tapered structure) or b) without other comonomers, which can be added after quantitative or close to quantitative conversion of vinylsilane to generate block structure. Additionally, several (n) dosing steps of vinylsilane compound of Formula 1 in variable proportions can be made at defined degrees of conversion of total monomer to generate n tapered or block structure elements within the polymer chain. After quantitative or close to quantitative conversion of monomers, a final addition of vinylsilane (2) or a chain-end modifying agent (as defined above) or coupling agent (as defined above) (3) can be used to generate block structure or another functionalization or coupling at polymer end.

(4) Several (n) dosing steps of vinylsilane compound of Formula 1 in variable proportions can be made at defined degrees of conversion of total monomer to generate n (tapered or block) structure elements within the polymer chain. After quantitative or close to quantitative conversion of monomers, a final addition of vinylsilane (2) or a chain-end modifying agent (as defined above) or coupling agent (as defined above) (3) can be used to generate block structure or another functionalization or coupling at polymer end.

(5) Dosing of vinylsilane compound of Formula 1 before addition of main amount of initiator a) together with main amounts of comonomers (tapered structure) or b) without other comonomers, which can be added after quantitative or close to quantitative conversion of vinylsilane to generate block structure. After quantitative or close to quantitative conversion of monomers, chain-end modifying agent (as defined above) or coupling agent (as defined above) can be added to functionalize or couple polymer chains.

Polymer

The elastomeric polymer according to the fourth aspect of the invention is obtainable by the process of the present invention, namely by polymerizing at least one conjugated diene monomer, a vinylsilane compound of Formula 1 (including Formula 6) and optionally one or more aromatic vinyl monomers in the presence of an initiator compound. The polymer of the invention may be a statistical, block or tapered copolymer, or an alpha- or alpha, omega-modified polymer where the vinylsilane of Formula 1 is incorporated in the polymer chain by means of its vinyl function. The polymer may be linear or branched.

Specifically, the vinylsilane compound of Formula 1 may be incorporated in the polymer chain (backbone; represented by the wavy line) as follows:

(I) Insertion via vinyl moiety only:

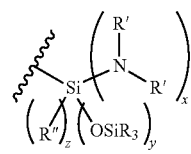

I where the parameters are as defined for Formula 1;

(II) Insertion via vinylsilane moiety, e.g. for R"=Me and z=1:

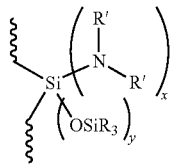
(II)

where the parameters are as defined for Formula 1.

In addition, when the polymerization process is terminated, e.g., by steam stripping, the following (partial) hydrolytic products are conceivable as well:

(III) Hydrolysis product of (I):

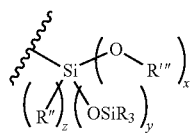
(III)

where R'" is selected from hydrogen, methyl, ethyl and —Si(OSiR$_3$)$_y$(R")$_z$(polymer) and the other parameters are as defined for Formula 1;

(IV) Hydrolysis product of (II):

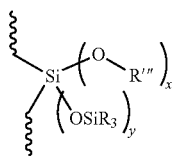
(IV)

where R'" is selected from hydrogen, methyl, ethyl and —Si(OSiR$_3$)$_y$(R")$_z$(polymer) and the other parameters are as defined for Formula 1.

In preferred embodiments, the polymer of the invention is an SSBR (solution styrene butadiene rubber) with a preferred vinyl content of 15-80%, more preferred 30-75%, most preferred 40-70% (dependent on the specific application), a styrene content (depending on the specific application) in total amounts of 40-70 wt. %, or 15-40 wt. %, or 2-15 wt. %; a PBR (polybutadiene rubber) with a vinyl content of <15%; or 15-40%, or 40-80%; a PIR (polyisoprene rubber); an SSIR (solution styrene isoprene rubber); or an SSIBR (solution styrene isoprene butadiene rubber); more preferably an SSBR or PBR; even more preferably an SSBR, each being modified by incorporation of the vinylsilane compound of Formula 1. In case of an SSBR, the elastomeric polymer is characterized by a glass transition temperature (Tg, determined by DSC) of −90 to 0° C., preferably −80 to −5° C., more preferably −70 to −10° C. The most preferred Tg for truck tire applications is −70 to −40° C., and the most preferred Tg for passenger car tire applications is −40 to −10° C.

Non-Cured Polymer Composition

The non-cured polymer composition of the fifth aspect of the present invention comprises the elastomeric polymer of the invention and one or more further components selected from (i) components which are added to or formed as a result of the polymerization process used for making said polymer and (ii) components which remain after solvent removal from the polymerization process. In particular, such components (i) and (ii) can be one or more components selected from oils (extender oils), fillers, stabilizers and further polymers (which are not the polymers of the invention). In one embodiment, the polymer composition additionally comprises one or more vulcanizing agents.

In one embodiment, the non-cured (non-crosslinked or unvulcanized) polymer composition is obtained by conventional work-up of the reaction mixture obtained in the polymerization process. Work-up means the removal of the solvent using steam stripping or vacuum evaporation techniques.

In another embodiment, the non-cured polymer composition of the invention is obtained as a result of a further mechanical mixing process involving the worked-up reaction mixture (including the polymer of the invention), preferably in the form of a rubber bale (i.e. the product of a conventional compounding process in an internal mixer and/or by means of a two-roll mill), and at least one filler. Further details are described in F. Rothemeyer, F. Sommer, Kautschuk Technologie: Werkstoffe—Verarbeitung—Produkte, 3rd ed., (Hanser Verlag, 2013) and references cited therein.

The following components are usually added in non-cured compositions used in tires: Extender oils, stabilizers, fillers, further polymers.

(Extender) Oils

In one embodiment, the polymer composition of the present invention comprises the elastomeric polymer of the invention in combination with one or more oils, especially mineral oils. For representative examples and classification of oils see WO 2009/148932 and US 2005/0159513, each of which is incorporated herein by reference in its entirety. Such oils include, for instance, conventionally known extender oils such as aromatic, naphthenic and paraffinic extender oils, for example MES (mild extraction solvate), TDAE (treated distillate aromatic extract), rubber-to-liquid (RTL) oils, biomass-to-liquid (BTL) oils, factices, extender resins or liquid polymers (such as liquid BR) having a median molecular weight (determined via GPC according to BS ISO 11344:2004) of from 500 to 20000 g/mol. When using a mineral oil as the extender oil, it is preferably one or more selected from DAE (Destillated Aromatic Extracts), RAE (Residual Aromatic Extract), TDAE, MES and naphthenic oils. The aforementioned oils comprise different concentrations of polycyclic aromatic compounds, parafinics, naphthenics and aromatics, and have different glass transition temperatures. The above mentioned types of oil have been characterized in "Kautschuk. Gummi Kunststoffe", vol. 52, pages 799-805. In some embodiments, MES, RAE and TDAE are preferred extender oils for rubber.

The one or more oils can be added to the polymer prior to or after the termination of the polymerization process. When the extender oil is added to the polymer solution, the timing of addition should preferably be after modification of the polymer or termination of the polymerization, for example after the addition of the modifying agent or polymerization termination agent. After the addition of extender oil, the oil-extended polymer composition can be obtained by separating any polymerization solvent from the polymer by means of a direct drying method or steam stripping, drying the rubber using a vacuum dryer, hot-air dryer, roller and the like.

The polymer composition may have contain one or more oils in a total amount of from 0 to 70 phr, preferably 0.1 to 60 phr, more preferably 0.1 to 50 phr. When liquid polymers are used as extender oils in the polymer composition of the present invention, they are not taken into account when calculating the composition of the polymer matrix.

In another embodiment, the oil is added to the "solvent-free" polymer in a mechanical mixer together with at least one filler, preferably with at least one filler and at least one further polymer.

Fillers

The polymer composition of the invention, which optionally comprises one or more extender oils as defined above, may further comprise one or more fillers. Filler can be added to the polymer prior to or after the termination of the polymerization process. Examples of suitable fillers include carbon black (including electroconductive carbon black), carbon nanotubes (CNT) (including discrete CNT, hollow carbon fibers (HCF) and modified CNT carrying one or more functional groups, such as hydroxyl, carboxyl and carbonyl groups), graphite, graphene (including discrete graphene platelets), silica, carbon-silica dual-phase filler, clays (layered silicates, including exfoliated nanoclay and organoclay), calcium carbonate, magnesium carbonate, magnesium oxide, titanium dioxide, rubber gels, lignin, amorphous fillers, such as glass particle-based fillers, starch-based fillers, and combinations thereof. Further examples of suitable fillers are described in WO 2009/148932, which is fully incorporated herein by reference.

Any type of carbon black conventionally known to a person of skill in the art may be used. In one embodiment, the carbon black has an iodine number according to ASTM D 1510 of 20 to 250 mg/g, preferably 30 to 180 mg/g, more preferably 40 to 180 mg/g, and even more preferably 40 to 130 mg/g, and a DBP number according to ASTM D 2414 of 80 to 200 ml/100 g, preferably 100 to 200 ml/100 g, more preferably 115 to 200 ml/100 g (the DBP number determines the specific absorption volume of carbon black or of any bright filler by means of dibutyl phthalate).

Any type of silica conventionally known to a person of skill in the art and suitable as filler for tire rubber blends may be used. It is particularly preferred to use highly dispersed, precipitated silica having an nitrogen surface area (BET surface area; according to DIN ISO 9277 and DIN 66132) of 35 to 350 m$^2$/g, preferably 35 to 260 m$^2$/g, more preferably 100 to 260 m$^2$/g and even more preferably 130 to 235 m$^2$/g, and having a CTAB surface area (according to ASTM D 3765) of 30 to 400 m$^2$/g, preferably 30 to 250 m$^2$/g, more preferably 100 to 250 m$^2$/g and even more preferably 125 to 230 m$^2$/g. Such silica results, e.g. in rubber blends for tire treads, to particularly beneficial physical properties of the vulcanizates. In addition, it may bring about advantages in the processing of the blend, namely by reducing the time required for blending, while maintaining product properties, thus improving productivity. Useful silicas include those of the type Ultrasil® VN3 (trademark of Evonik Industries) as well as highly dispersed types, so-called HD silicas (e.g. Zeosil® 1165 MP of Rhodia).

Stabilizers

One or more stabilizers ("antioxidants") can optionally be added to the polymer prior to or after the termination of the polymerization process to prevent the degradation of the elastomeric polymer by molecular oxygen. Antioxidants based on sterically hindered phenols, such as 2,6-di-tert-butyl-4-methylphenol, 6,6'-methylenebis(2-tert-butyl-4-methylphenol), Iso-octyl-3-(3,5-di-tert-butyl-4-hydroxyphenyl) propionate, hexamethylenebis[3-(3,5-di-tert-butyl-4-hydroxy-phenyl)propionate], octadecyl-3-(3,5-di-tert-butyl-4-hydroxyphenyl) propionate, isotridecyl-3-(3,5-di-tert-butyl-4-hydroxyphenyl) propionate, 1,3,5-trimethyl-2,4,6-tris(3,5-di-tert-butyl-4-hydroxybenzyl) benzene, 2,2'-ethylidenebis-(4,6-di-tert-butylphenol), tetrakis[methylene-3-(3,5-di-tert-butyl-4-hydroxyphenyepropionate]methane, 2-[1-(2-hydroxy-3,5-di-tert-pentyl-phenyl)ethyl]-4,6-di-tert-pentylphenyl acrylate and 2-tert-butyl-6-(3-tert-butyl-2-hydroxy-5-methylbenzyl)-4-methylphenyl acrylate, and antioxidants based on thio-esters, such as 4,6-bis(octylthiomethyl)-o-cresol and pentaerythrityl tetrakis(3-laurylthiopropionate), are typically used. Further examples of suitable stabilizers can be found in F. Rothemeyer, F. Sommer, Kautschuk Technologie, 2$^{nd}$ ed., (Hanser Verlag, 2006) pages 340-344, and references cited therein.

Further Polymers

Apart from polymer of the invention, extender oil(s), filler(s), etc., the polymer composition of the invention may additionally contain further polymer, especially further elastomeric polymer. Further polymers may be added as solution to a solution of the inventive polymer prior to work up of the polymer blend or may be added during a mechanical mixing process, e.g. in a Brabender mixer.

Further (elastomeric) polymers as referred to herein are elastomeric polymers which are not in accordance with the polymer of the invention, i.e. which do not contain repeating units derived from the vinylsilane compound of Formula 1.

Vulcanizing Agents and Vulcanizing Accelerators

The polymer composition of the invention may optionally further comprise a least one vulcanizing agent. Any vulcanizing agent conventionally used in the manufacture of rubber products can be used in the invention, and a combination of two or more vulcanizing agents may be used.

Sulfur, sulfur-containing compounds acting as sulfur donors such as dithiols, sulfur accelerator systems and peroxides are the most common vulcanizing agents. Examples of sulfur-containing compounds acting as sulfur donors include dithiodimorpholine (DTDM), tetramethylthiuram disulfide (TMTD), tetraethyl thiuram disulfide (TETD) and dipentamethylene thiuram tetrasulfide (DPTT). Examples of sulfur accelerators include amine derivates, guanidine derivates, aldehydeamine condensation products, thiazoles, xanthogenates, thiuram sulfides, dithiocarbamates and thiophosphates. It is preferably to use one or more sulfonamide accelerators seleceted from N-cyclohexyl 2-benzothiazol sulfenamide (CBS), N,N-dicyclohexyl benzothiazole 2-sulfenamide (DCBS), benzothiazyl 2-sulfenemorpholide (MBS) and N-tert-butyl 2-benzothiazyl sulfenamide (TBBS). Further crosslinking systems such as available under the trade names Vulkuren® (1,6-bis(N, N-dibenzyl thiocarbamoyldithio)-hexane; Lanxess), Duralink® or Perkalink® (1,3-bis(citraconimidomethyl)benzene; Lanxess) or disclosed in WO 2010/049261 may be added to the polymer composition. Examples of peroxides include di-tert.-butyl-peroxides, di-(tert.-butyl-peroxy-trimethyl-cyclohexane), di-(tert.-butyl-peroxy-isopropyl-)benzene, dichloro-benzoylperoxide, dicumylperoxides, tert.-butylcumyl-peroxide, dimethyl-di(tert.-butyl-peroxy)hexane, dimethyl-di(tert.-butyl-peroxy)hexine and butyl-di(tert.-butyl-peroxy)valerate (*Rubber Handbook, SGF, The Swedish Institution of Rubber Technology* 2000).

A vulcanizing accelerator of the sulfene amide-type, guanidine-type or thiuram-type can be used together with a vulcanizing agent as required.

In addition, the polymer composition of the invention may contain conventional additives and vulcanization auxiliaries in proportions conventionally used. Such additives include:

a) aging inhibitors such as N-phenyl N'-(1,3-dimethylbutyl)-p-phenylenediamine (6PPD), N,N'-diphenyl-p-phenylenediamine (DPPD), N,N'-ditolyl-p-phenylenediamine (DTPD), N-isopropyl N'-phenyl-p-phenylenediamine (IPPD), 2,2,4-trimethyl 1,2-dihydrochinolin (TMQ), b) activators such as zinc oxide and fatty acids (e.g. stearic acid), c) waxes, d) resins, especially adhesive resins, e) mastication additives such as 2,2'-dibenzamidodiphenyldisulfide (DBD) and f) processing additives such as zinc soaps and fatty acid esters and their derivatives.

Zinc oxide (zinc white) is preferably used as a component of the sulfur accelerator system.

A vulcanizing agent is typically added to the polymer composition in an amount of from 0.5 to 10 parts by weight or, in some embodiments, 1 to 6 parts by weight per 100 parts by weight of the total polymer. Examples of vulcanizing accelerators and amounts thereof added with respect to the total polymer are given in WO 2009/148932, which is incorporated herein by reference in its entirety.

Vulcanized Polymer Composition

The vulcanized polymer composition of the sixth aspect of the invention is obtained by vulcanizing a polymer composition of the invention comprising one or more vulcanizing agents, under conditions and with machinery conventionally known in the art.

Article Comprising Vulcanized Polymer Composition

Since the vulcanized polymer compositions of the invention exhibit low rolling resistance, low dynamic heat build-up and increased wet grip, they are well suited for use in manufacturing, e.g., tires or parts of tires including for example: tire treads, side walls and tire carcasses as well as other industrial products such as belts, hoses, vibration dampers and footwear components. Thus, the article of the seventh aspect of the present invention comprises at least one component formed from the vulcanized polymer composition of the invention. The article may be, for instance, a tire, a tire tread, a tire side wall, a tire carcass, a belt, a gasket, a seal, a hose, a vibration damper, a golf ball or a footwear component, such as a shoe sole.

Definitions

Alkyl groups as defined herein, whether as such or in association with other groups, such as alkylaryl or alkoxy, include both straight chain alkyl groups, such as methyl (Me), ethyl (Et), n-propyl (Pr), n-butyl (Bu), n-pentyl, n-hexyl, etc., branched alkyl groups, such as isopropyl, tert-butyl, etc., and cyclic alkyl groups, such as cyclohexyl.

Aryl groups as defined herein include phenyl, biphenyl and other benzenoid compounds. Aryl groups preferably contain only one aromatic ring and most preferably contain a $C_6$ aromatic ring.

Alkylaryl groups as defined herein refer to a combination of one or more aryl groups bound to one or more alkyl groups, for example in the form of alkyl-aryl, aryl-alkyl, alkyl-aryl-alkyl and aryl-alkyl-aryl. Alkylaryl groups preferably contain only one aromatic ring and most preferably contain a $C_6$ aromatic ring.

The present invention will be explained in more detail by way of examples, which are not intended to be limiting the present invention.

EXAMPLES

Preparation of Vinylsilane Compound of Formula 1—General Recipe

A solution of dihalovinylsilane or neat dihalovinylsilane (1.0 equiv.) is added dropwise to a solution of trialkylsilanol or triarylsilanol (0.9-2 equiv.) and a suitable proton scavenger (1.5-5 equiv.) in a hydrocarbon solvent at 0-50° C. The mixture is stirred for several hours (preferably more than 1 h) at 0-50° C. Then the secondary amine compound (1.0 equiv.) is added, and the mixture is stirred for several hours at a temperature of between 0° C. and the reflux temperature of the solvent. After filtration, the solvent is removed under reduced pressure. Purification, preferably by vacuum distillation or recrystallization, provides the desired vinylsilane compound.

In the above general recipe for producing a vinylsilane of Formula 1, the order of addition of the components can be modified.

Preparation and Characterization of Specific Vinylsilane Compounds

4-[(Dimethyl(vinyl)silyl]morpholine (Mod 1)

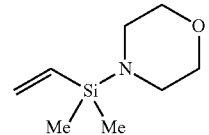

bp=85° C. (37 mbar). $^1$H NMR (400 MHz, 20° C., $C_6D_6$): δ=6.05 (dd, J=20.0 Hz, J=14.7 Hz, 1H), 5.91 (dd, J=14.7 Hz, J=4.2 Hz, 1H), 5.67 (dd, J=20.0 Hz, J=4.2 Hz, 1H), 3.44-3.41 (m, 4H), 2.68-2.66 (m, 4H), 0.04 (s, 6H) ppm. $^{13}$C NMR (101 MHz, 20° C., $C_6D_6$): δ=138.71 (CH, vinyl), 132.49 ($CH_2$, vinyl), 68.61 (2 $CH_2$), 45.92 (2 $CH_2$), −2.77 (2 $CH_3$) ppm. GC-MS (EI, 70 eV): m/z (%)=171 ($M^+$, 70), 156 ($M^+$−$CH_3$, 32), 130 (19), 113 (30), 85 ($C_4H_9Si^+$, 100), 59 (65).

(Tert-butyldimethylsiloxy)methyl-4-morpholino(vinyl)silane (Mod 2)

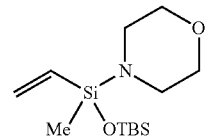 [SMILES: C=C[Si](C)(O[Si](C)(C)C(C)(C)C)N1CCOCC1]

Dichlorovinylmethylsilane (15.2 g, 108 mmol, 1.0 equiv.) was added dropwise to a solution of TBSOH (tert-butyldimethylsilanol, 14.2 g, 108 mmol, 1.0 equiv.) and triethylamine (22.9 g, 226 mmol, 2.1 equiv.) in dichloromethane (DCM; 150 ml) at room temperature. The mixture was stirred for 2 h at room temperature. Then morpholine (9.38 g, 108 mmol, 1.0 equiv.) was added and the mixture was stirred for a further 18 h. After filtration the solvent was removed under reduced pressure and distillation at 1 mbar furnished Mod 2 (18.6 g, 64.7 mmol, 60%) as a colorless liquid.

bp=95-97° C. (1 mbar). $^1$H NMR (400 MHz, 20° C., $C_6D_6$): δ=6.02 (dd, J=19.3 Hz, J=14.7 Hz, 1H), 5.94 (dd, J=14.8 Hz, J=5.4 Hz, 1H), 5.83 (dd, J=19.0 Hz, J=5.4 Hz, 1H), 3.47 (t, J=4.6 Hz, 4H), 2.85-2.75 (m, 4H), 0.95 (s, 9H), 0.11 (s, 3H), 0.07 (s, 6H) ppm. $^{13}$C NMR (101 MHz, 20° C., C$_6$D$_6$): δ=137.06 (CH, vinyl), 133.73 (CH$_2$, vinyl), 68.56 (2 CH$_2$), 45.55 (2 CH$_2$), 25.92 (3 CH$_3$), 18.38 (C), −2.46 (CH$_3$), −2.75 (2 CH$_3$) ppm. GC-MS (EI, 70 eV): m/z (%)=287 (M$^+$, 6), 272 (M$^+$–CH$_3$, 9), 230 (M$^+$–C$_4$H$_9$, 100), 202 (4), 174 (6), 145 (39), 117 (16), 70 (22).

1-[(tert-butyldimethylsiloxy)methyl(vinyl)silyl]-4-methylpiperazine

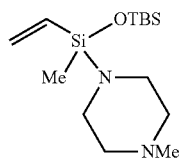 [SMILES: C=C[Si](C)(O[Si](C)(C)C(C)(C)C)N1CCN(C)CC1]

A solution of TBSOH (tert-butyldimethylsilanol, 4.68 g, 35.4 mmol, 1.0 equiv.) in ethylacetate (20 ml) was added dropwise to a solution of dichloromethylvinylsilane (5.0 g, 35 4 mmol, 1.0 equiv.) and triethylamine (7.15 g, 70.8 mmol, 2.0 equiv.) in ethyl acetate (70 ml) at room temperature. The mixture was stirred for 2.5 h at room temperature. Then N-methylpiperazine (3.72 g, 37.2 mmol, 1.05 equiv.) was added and the mixture was stirred for a further 20 h. After filtration the solvent was removed under reduced pressure and distillation at 6 mbar furnished modifier (8.57 g, 28.5 mmol, 81%) as a colorless liquid.

bp=113-115° C. (6 mbar). $^1$H NMR (400 MHz, 20° C., C$_6$D$_6$): δ=6.09 (dd, J=19.7 Hz, J=14.8 Hz, 1H), 5.95 (dd, J=14.8 Hz, J=4.7 Hz, 1H), 5.88 (dd, J=19.7 Hz, J=4.6 Hz, 1H), 3.03-2.95 (m, 4H), 2.20-2.11 (m, 4H), 2.12 (s, 3H), 0.96 (s, 9H), 0.17 (s, 3H), 0.10 (s, 6H) ppm. $^{13}$C NMR (101 MHz, 20° C., C$_6$D$_6$): δ=137.53 (CH, vinyl), 133.44 (CH$_2$, vinyl), 57.11 (2 CH$_2$), 46.98 (CH$_3$), 45.26 (2 CH$_2$), 25.98 (3 CH$_3$), 18.42 (C), −2.15 (CH$_3$), −2.68 (2 CH$_3$) ppm. GC-MS (EI, 70 eV): m/z (%)=300 (M$^+$, 100), 243 (M$^+$—C$_4$H$_9$, 65), 188 (13), 133 (35), 99 (8), 70 (23).

(Tertbutyldimethylsiloxy)(dibutylamino)methyl(vinyl)silane

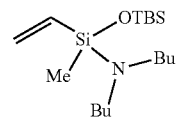

A solution of TBSOH (tert-butyldimethylsilanol, 4.68 g, 35.4 mmol, 1.0 equiv.) in dichloromethane (20 ml) was added dropwise to a solution of dichloromethylvinylsilane (5.0 g, 35.4 mmol, 1.0 equiv.) and triethylamine (7.16 g, 70.8 mmol, 2.05 equiv.) in DCM (70 ml) at room temperature. The mixture was stirred for 2.5 h at room temperature. Then dibutylamine (4.80 g, 37.2 mmol, 1.05 equiv.) was added and the mixture was stirred for a further 20 h. After filtration the solvent was removed under reduced pressure and distillation at 4 mbar furnished modifier (7.91 g, 24.0 mmol, 68%) as a colorless liquid.

bp=133-135° C. (4 mbar). $^1$H NMR (400 MHz, 20° C., C$_6$D$_6$): δ=6.17 (dd, J=20.1 Hz, J=14.8 Hz, 1H), 5.96 (dd, J=14.8 Hz, J=4.3 Hz, 1H), 5.86 (dd, J=20.0 Hz, J=4.3 Hz, 1H), 2.84 (dd, J=8.4 Hz, J=6.9 Hz, 4H), 1.46 (pent, J=7.5 Hz, 4H), 1.25 (sext, J=7.4 Hz, 4H), 0.99 (s, 9H), 0.91 (t, J=7.4 Hz, 6H), 0.25 (s, 3H), 0.13 (s, 6H) ppm. $^{13}$C NMR (101 MHz, 20° C., C$_6$D$_6$): δ=138.60 (CH, vinyl), 132.66 (CH$_2$, vinyl), 46.12 (2 CH$_2$), 32.86 (2 CH$_2$), 26.02 (3 CH$_3$), 20.73 (2 CH$_2$), 18.50 (C), 14.38 (2 CH$_3$), −1.40 (CH$_3$), −2.64 (CH$_3$), −2.65 (CH$_3$) ppm. GC-MS (EI, 70 eV): m/z (%)=329 (M$^+$, 4), 315 (M$^+$, 12), 286 (100), 244 (7), 215 (2), 186 (12), 133 (75), 103 (7), 73 (18).

(Tertbutyldimethylsiloxy)(diethylamino)methyl(vinyl)silane

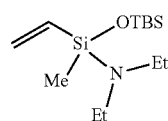

A solution of TBSOH (tert-butyldimethylsilanol, 4.68 g, 35.4 mmol, 1.0 equiv.) in ethyl acetate (20 ml) was added dropwise to a solution of dichloromethylvinylsilane (5.0 g, 35.4 mmol, 1.0 equiv.) and triethylamine (7.15 g, 70.8 mmol, 2.0 equiv.) in ethyl acetate (70 ml) at room temperature. The mixture was stirred for 3 h at room temperature. Then diethylamine (2.58 g, 35.4 mmol, 1.0 equiv.) was added and the mixture was stirred for a further 4 h. After filtration the solvent was removed under reduced pressure and distillation at 4 mbar furnished modifier (6.43 g, 23.5 mmol, 66%) as a colorless liquid.

bp=78-80° C. (4 mbar). $^1$H NMR (400 MHz, 20° C., C$_6$D$_6$): δ=6.15 (dd, J=20.0 Hz, J=14.8 Hz, 1H), 5.95 (dd, J=14.8 Hz, J=4.4 Hz, 1H), 5.86 (dd, J=20.0 Hz, J=4.3 Hz, 1H), 2.84 (q, J=7.0 Hz, 4H), 0.99 (t, J=7.0 Hz, 6H), 0.98 (s, 9H), 0.21 (s, 3H), 0.11 (s, 6H) ppm. $^{13}$C NMR (101 MHz, 20° C., C$_6$D$_6$): δ=138.47 (CH, vinyl), 132.72 (CH$_2$, vinyl), 39.80 (2 CH$_2$), 25.99 (3 CH$_3$), 18.45 (C), 16.04 (2 CH$_3$), −1.54 (CH$_3$), −2.70 (2 CH$_3$) ppm. GC-MS (EI, 70 eV): m/z (%)=273 (M$^+$, 8), 258 (M$^+$–CH$_3$, 100), 216 (48), 186 (5), 158 (59), 145 (71), 119 (29), 73 (28).

(Tertbutyldimethylsiloxy)(dimethylamino)methyl(vinyl)silane

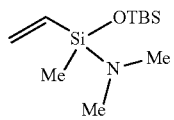

TBSOH (tert-butyldimethylsilanol, 4.69 g, 35.4 mmol, 1.0 equiv.) was added dropwise to a solution of dichloromethylvinylsilane (5.0 g, 35.4 mmol, 1.0 equiv.) and triethylamine (7.53 g, 74.4 mmol, 2.1 equiv.) in ethyl acetate (60 ml) at room temperature. The mixture was stirred for 3 h at this temperature, then dimethylamine (1.76 g, 38.9 mmol, 1.1 equiv.) was added at 0° C. and the mixture was stirred for a further 18 h. After filtration the solvent was removed under reduced pressure and distillation at 24 mbar furnished modifier (6.06 g, 24.7 mmol, 70%) as a colorless liquid.

bp=89-90° C. (24 mbar). $^1$H NMR (400 MHz, 20° C., C$_6$D$_6$): δ=6.11 (dd, J=19.8 Hz, J=14.8 Hz, 1H), 5.96 (dd, J=14.8 Hz, J=4.5 Hz, 1H), 5.87 (dd, J=19.8 Hz, J=4.5 Hz, 1H), 2.47 (s 6H), 0.97 (s, 9H), 0.19 (s, 3H), 0.09 (s, 6H) ppm. $^{13}$C NMR (101 MHz, 20° C., C$_6$D$_6$): δ=137.56 (CH, vinyl), 133.27 (CH$_2$, vinyl), 37.56 (2 CH$_3$), 25.92 (3 CH$_3$), 18.42 (C), −2.15 (CH$_3$), −2.84 (2 CH$_3$) ppm. GC-MS (EI, 70 eV): m/z (%)=245 (M$^+$, 6), 230 (M$^+$−CH$_3$, 10), 188 (99), 145 (100), 105 (7), 73 (20).

(Tertbutyldimethylsiloxy)methyl(propyl(trimethylsilyl)amino)(vinyl)silane

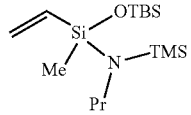

TBSOH (tert-butyldimethylsilanol, 3.99 g, 30.2 mmol, 1.0 equiv.) was added dropwise to a solution of dichloromethylvinylsilane (4.26 g, 30.2 mmol, 1.0 equiv.) and triethylamine (9.20 g, 90.9 mmol, 3.0 equiv.) in DCM (40 ml) at rt. The mixture was stirred for 3 h at room temperature. Then propylamine (1.96 g, 33.2 mmol, 1.1 equiv.) was added and the mixture was stirred for a further 3.5 h at rt. Afterwards chlorotrimethyl silane (4.92 g, 45.3 mmol, 1.5 equiv.) was added and the reaction mixture was stirred for a further 18h at rt and 1 h at 35° C. After filtration the solvent was removed under reduced pressure and distillation at 4 mbar furnished modifier (3.52 g, 10.6 mmol, 35%) as a colorless liquid.

bp=102-105° C. (4 mbar). $^1$H NMR (400 MHz, 20° C., C$_6$D$_6$): δ=6.20 (dd, J=20.2 Hz, J=14.8 Hz, 1H), 5.90 (dd, J=14.8 Hz, J=4.0 Hz, 1H), 5.79 (dd, J=20.2 Hz, J=4.0 Hz, 1H), 2.81-2.77 (m, 2H), 1.51-1.41 (m, 2H), 0.98 (s, 9H), 0.76 (t, J=7.4 Hz, 3H), 0.28 (s, 3H), 0.21 (s, 9H), 0.12 (s, 6H) ppm. $^{13}$C NMR (101 MHz, 20° C., C$_6$D$_6$): δ=140.33 (CH, vinyl), 132.27 (CH$_2$, vinyl), 47.04 (CH$_2$), 28.67 (CH$_2$), 26.06 (3 CH$_3$), 18.51 (C), 11.46 (CH$_3$), 2.11 (3 CH$_3$), 0.55 (CH$_3$), −2.54 (CH$_3$), −2.57 (CH$_3$) ppm. GC-MS (EI, 70 eV): m/z (%)=331 (M$^+$, 17), 302 (M$^+$−C$_2$H$_5$, 100), 274 (20), 230 (5), 204 (4), 159 (15), 133 (27), 73 (45).

Polymerization

Example A1 (Reference Example)

Cyclohexane (2324.5 g), butadiene (316.7 g) and styrene (86.1 g) were charged to a deaerated 5 1 reactor and the stirred mixture was heated up to 40° C. Then TMEDA (4.1 mmol) and compound Mod 1 (2.8 g) were added and n-butyllithium was charged dropwise to react the impurities until the color of the reaction mixture changed to yellowish (titration). After that the recipe amount of n-butyllithium (2.03 mmol) corresponding to the target molecular weight of the polymer was charged immediately via pump to start the polymerization. The start time of the charge of the main amount of n-butyllithium was used as the start time of the polymerization. In parallel the temperature was adjusted by heating or cooling of the reactor walls beginning with the charge of the main amount of n-butyllithium to the final polymerization temperature of 60° C. for 80 min. Then butadiene (1.55 g) was charged followed by SnCl$_4$ (1.35 g) and 50 g cyclohexane via cylinder. The reaction was allowed to complete within 15 minutes followed by the last addition of butadiene (5.8 g). The reaction was terminated by addition of methanol (4 mmol). The polymer solution was stabilized with Irganox 1520D (1.02 g), the polymer recovered by steam stripping and dried to a content of residual volatiles of <0.6%. The glass transition temperature of the polymer was −22.4° C. The complete data set of the sample is given in Table 1.

Example A2 (In Accordance With Invention)

Example A1 was repeated, yet replacing compound Mod 1 with compound Mod 2.

Example B1 (Reference Example)

Cyclohexane (2309 g), butadiene (314.6 g) and styrene (85.6 g) were charged to a deaerated 5 1 reactor and the stirred mixture was heated up to 40° C. Then TMEDA (4.1 mmol) and compound Mod 1 (1.4 g) were added and n-butyllithium was charged dropwise to react the impurities until the color of the reaction mixture changed to yellowish (titration). After that the recipe amount of n-butyllithium (2.02 mmol) corresponding to the target molecular weight of the polymer was charged immediately via pump to start the polymerization. The start time of the charge of the main amount of n-butyllithium was used as the start time of the polymerization. In parallel the temperature was adjusted by heating or cooling in the reactor walls beginning with the charge of the main amount of n-butyllithium to the final polymerization temperature of 60° C. for 80 min. Then butadiene (1.54 g) was charged followed by SnCl$_4$ (1.34 g) and 50 g cyclohexane via cylinder. The reaction was allowed to complete within 15 minutes followed by the last addition of butadiene (5.8 g). After 5 minutes chain end modifier 3-methoxy-3,8,8,9,9-pentamethyl-2-oxa-7-thia-3,8-disiladecane (compound 2f, 0.51 g) was added and the reaction mixture was stirred for a further 20 minutes. Then the reaction was terminated by addition of methanol (2 mmol). The polymer solution was stabilized with Irganox 1520D (1 g), the polymer recovered by steam stripping and dried to a content of residual volatiles of <0.6%. The glass transition temperature of the polymer was −24.1° C. The complete data set of the sample is given in Table 1.

Example B2 (In Accordance With Invention)

Example B1 was repeated, yet replacing compound Mod 1 with compound Mod 2.

Comparative Example 1

Cyclohexane (4624 g), butadiene (687.0 g) and styrene (187 g) were charged to a deaerated 101 reactor and the stirred mixture was heated up to 40° C. Then TMEDA (8.87 mmol) was added and n-butyllithium was charged dropwise to react the impurities until the color of the reaction mixture changed to yellowish (titration). After that the recipe amount of n-butyllithium (4.43 mmol) corresponding to the target molecular weight of the polymer was charged immediately via pump to start the polymerization. The start time of the charge of the main amount of n-butyllithium was used as the start time of the polymerization. In parallel the temperature was adjusted by heating or cooling the reactor walls beginning with the charge of the main amount of n-butyllithium to the final polymerization temperature of 60° C. for 80 min. Then butadiene (3.5 g) was charged followed by SnCl$_4$ (2.9 g) and 20 g cyclohexane via cylinder. The reaction was allowed to complete within 10 minutes followed by the last addition of butadiene (12.7 g). After 5 minutes chain end modifier 2f (1.12 g) was added and the reaction mixture was stirred for a further 20 minutes. Then the reaction was terminated with charge of methanol (4.5 mmol). The polymer solution was stabilized with Irganox 1520D (2.2 g), the polymer recovered by steam stripping and dried to a content of residual volatiles of <0.6%. The complete data set of the sample is given in Table 1.

compared to Example A1 and Comparative Example 1, as reflected by tan δ at 0° C., and still showed better handling characteristic at low temperatures, as reflected by low values of E' at −25° C. The stability of Example A2 (reflected by higher stiffness at high temperatures (E' 60° C.)) is on par with Comparative Example 1 and better than Example A1.

TABLE 1

Polymerization details

|  | Ex. A1 | Ex. A2 | Ex. B1 | Ex. B2 | Comp. Ex 1 |
|---|---|---|---|---|---|
| Cyclohexane/g | 2324 | 2323 | 2309 | 2308 | 4624 |
| Butadiene/g | 319.4 | 324 | 324.6 | 323.8 | 699 |
| Styrene/g | 86.1 | 86.2 | 86.3 | 86.1 | 186 |
| Vinyl compound/mmol | 16.6 Mod 1 | 16.2 Mod 2 | 8.08 Mod 1 | 8.07 Mod 2 | — |
| TMEDA/mmol | 4.09 | 4.06 | 4.09 | 4.03 | 8.85 |
| nBuLi/mmol | 2.07 | 2.03 | 2.02 | 2.02 | 4.44 |
| $SnCl_4$/mmol | 0.145 | 0.141 | 0.145 | 0.140 | 0.294 |
| Compound 2f/mmol | — | — | 1.81 | 1.85 | 3.81 |
| Tg/° C. | −22.4 | −22.8 | −24.1 | −22.7 | — |
| Mp/kg/mol | 307 | 323 | 307 | 306 | 305 |
| Vinyl content/% | 63.3 | 63.1 | 61.9 | 61.9 | 61.8 |
| Styrene content | 21.0 | 21.0 | 21.1 | 20.9 | 20.4 |
| $M_L$ | 60.3 | 70.7 | 53.1 | 52.9 | 60.3 |

Compound 2f = 3-methoxy-3,8,8,9,9-pentamethyl-2-oxa-7-thia-3,8-disiladecane

Compounding for Series 1 and 2

Compounding for Series 1 and 2 was done in a 2-step-mixing process according to the following recipe with a 350 ml Banbury internal lab mixer.

TABLE 2

Recipe for Series 1 and 2

| Mixing stage | Formulation | phr |
|---|---|---|
| 1 | Polymer | 80.0 |
|  | BUNA ™ cis 132-Schkopau[1] | 20.0 |
|  | Ultrasil ® 7000 GR[2] | 80.0 |
|  | Si 75 ®[3] | 6.9 |
|  | TDAE VivaTec500[4] | 20.0 |
|  | Stearic acid | 1.0 |
|  | Zinc oxide | 2.5 |
|  | Dusantox ® 6PPD[5] | 2.0 |
|  | Wax Antilux ® 654[6] | 1.5 |
| 2 | Sulfur | 1.4 |
|  | TBBS[7] | 1.5 |
|  | DPG[8] | 1.5 |

[1]Styron Deutschland GmbH
[2]Evonik Industries; BET surface area ca. 170 m²/g
[3]Bis(triethoxysilylpropyl)disulfide; Evonik Industries
[4]Treated distilled aromatic extract; extender oil by Hansen & Rosenthal
[5]N-1,3-dimethylbutyl-N'-phenyl-p-phenylenediamine; Duslo
[6]Antisun and antiozonant wax; Rheinchemie (Lanxess)
[7]N-tert-butyl-2-benzothiazole sulfenamide
[8]1,3-diphenylguanidine Discussion of Series 1 and 2

In the case of higher polymer viscosity in Example A2, the compound viscosity (CML) after mixing in Series 1 was comparable to Example A1 and Comparative Example 1. Example A2 allowed better processing compared to Example A1 and Comparative Example 1. For the vulcanized samples, Example A2 showed mechanical stiffness comparable to Example A1, but better than Comparative Example 1 as reflected by Mod300. The polymer filler interaction, reflected by Mod300-Mod100, for Example A2 is as high as for Example A1 and better than Comparative Example 1. Example A2 gave better wet grip performance

TABLE 3

Series 1

|  | Ex. A1 | Ex. A2 | Comp. Ex. 1 |
|---|---|---|---|
| ML1 + 4 100° C. unmassed | 66.5 | 87.9 | 63.4 |
| CML1 + 4 | 96.4 | 99.7 | 89.3 |
| CML-ML | 29.9 | 11.8 | 25.9 |
| Mod100 [MPa] | 2.2 | 2.2 | 2.0 |
| Mod300 [MPa] | 13.5 | 13.4 | 10.7 |
| Mod300 − Mod100 [MPa] | 11.3 | 11.2 | 8.7 |
| E' −25° C. | 181.6 | 174.8 | 177.1 |
| E' 60° C. | 3.6 | 4.7 | 4.8 |
| Tan δ 0° C. | 0.427 | 0.467 | 0.424 |

In case of higher polymer viscosity in Example B2, the compound viscosity (CML) after mixing in Series 2 was comparable to Comparative Example 1 and lower than Example B1. Example B2 allowed better processing compared to Example B1 and Comparative Example 1. The mechanical properties of the vulcanizates are comparable to the reference systems. The polymer filler interaction, reflected by Mod300-Mod100, for Example B2 is in the same range. The wet grip performance, as reflected by tan δ at 0° C., for Example B2 is enhanced compared to Example B1 and Comparative Example 1.

TABLE 4

Series 2

|  | Ex. B1 | Ex. B2 | Comp. Ex. 1 |
|---|---|---|---|
| ML1 + 4 100° C. unmassed | 61.5 | 69.6 | 63.4 |
| CML1 + 4 | 94.9 | 90.1 | 89.5 |
| CML-ML | 33.4 | 20.5 | 26.1 |
| Mod100 [MPa] | 2.0 | 2.0 | 2.2 |
| Mod300 [MPa] | 12.2 | 11.4 | 11.2 |
| Mod300 − Mod100 [MPa] | 10.2 | 9.4 | 9.0 |
| E' −25° C. | 163.0 | 192.2 | 191.0 |
| E' 60° C. | 3.9 | 4.6 | 5.6 |
| Tan δ 0° C. | 0.363 | 0.407 | 0.397 |

Compounding for Series 3

Compounding for Series 3 was done similar to Series 1 and 2, yet using carbon black as filler, according the following recipe

TABLE 5

Recipe for Series 3

| Mixing stage | Formulation | phr |
|---|---|---|
| 1 | Polymer | 100.0 |
|  | IRB8 (⅔)[1] | 34.0 |
|  | IRB8 (⅓) | 16.0 |
|  | TDAE VivaTec500 | 15.0 |
|  | Stearic acid | 1.5 |
|  | Zinc oxide | 3.0 |
| 2 | Sulfur | 1.7 |
|  | TBBS[2] | 1.0 |

[1]Industry Reference Black, N330
[2]N-tert-butyl-2-benzothiazole sulfenamide

Discussion of Series 3

The mechanical properties of the vulcanizates are slightly improved over the reference systems. The polymer filler interaction, as reflected by Mod300-Mod100, for Examples A2 and B2 is bigger than for A1 or B1.

An enhanced ice grip, as reflected by tan δ @ −10° C., is observed for Examples A2 and B2 as compared to Comparative Example 1. Example A1 and B1 are worse than the reference (Comparative Example 1). Corresponding results were obtained for the rolling resistance: tan δ @ 60° C. is lower for Examples A2 and B2 (improvement as compared to Examples A1 and B1 and Comparative Example 1).

TABLE 6

Series 3

|  | Comp. Ex. 1 | Ex. A1 | Ex. B1 | Ex. A2 | Ex. B2 |
|---|---|---|---|---|---|
| Elongation at break [%] | 539 | 512 | 493 | 357 | 503 |
| Modulus 300 [MPa] | 10.2 | 9.8 | 10.5 | 12.5 | 10.9 |
| Mod300 − Mod100 [MPa] | 8.3 | 7.8 | 8.7 | 9.9 | 9.0 |
| E' @ −25° C. [MPa] | 2144 | 2452 | 2217 | 2506 | 2219 |
| E' @ −10° C. [MPa] | 106 | 84.8 | 44.2 | 101 | 77.5 |
| E' @ 0° C. [MPa] | 13.8 | 18.5 | 11.5 | 14.4 | 10.0 |
| E' @ 60° C. [MPa] | 4.43 | 4.93 | 3.99 | 5.54 | 3.92 |
| tan δ @ −10° C. | 1.269 | 1.169 | 1.197 | 1.277 | 1.361 |
| tan δ @ 60° C. | 0.163 | 0.206 | 0.151 | 0.148 | 0.134 |

Test Methods

The molecular weight analyses were carried out via SEC/RI using a HEWLETT PACKARD HP 1100. The eluent THF was degassed on-line. The solvent flow rate was 1.0 ml/min. 100 μL of polymer solution were injected per analysis. The analyses were carried out at 40° C. The molecular weights were initially calculated based on a polystyrene calibration and given in the tables as polystyrene. The real molecular weights (SSBR molecular weights) were determined by division by a factor derived from an earlier comparison between molecular weights from SEC/RI and SEC/MALLS. The value of the factor depends on the polymer composition (styrene and butadiene content). A factor of 1.52 was used for SSBR with 21% and 25% styrene. Mp (as SSBR) was used for the calculation of TMEDA molar ratios.

NMR-spectroscopy was performed on a BRUKER Avance 400 in a 5 mm BBO probe.

FTIR-spectroscopy measured in attenuated total reflection was used to determine the vinyl content and styrene content.

The glass transition temperature was determined using the DSC Q2000 under the following conditions:
Weight: ca. 10-12 mg
Sample container: Alu/S
Temperature range: (−140 . . . 80)° C.
Heating rate: 20 K./min or 5 K/min
Cooling rate: free cooling
Purge gas: 20 ml Ar/min
Cooling agent: liquid nitrogen Each sample was measured at least once. The measurements contain two heating runs. The 2nd heating run was used to determine the glass transition temperature.

Measurements of non-vulcanized rheological properties according to ASTM D 5289-95 were made using a rotorless shear rheometer (MDR 2000 E) to characterize cure characteristics. Test pieces were vulcanized to $t_{95}$ at 160° C. For rebound resilience tests the specimen were vulcanized to $t_{95+5}$ at 160° C. Tensile strength and moduli were measured according to ASTM D 412 on a Zwick Z010. DIN abrasion was measured according to DIN 53516 (1987-06-01). Rebound resilience (ISO 4662) was measured at 0° C., RT (20° C.) and 60°. Dynamic properties in terms of tan δ and E' at specified temperatures were measured using a dynamic spectrometer Eplexor 150N/500N manufactured by Gabo Qualimeter Testanlagen GmbH (Germany) applying a compression dynamic strain of 1% at a frequency of 2 Hz in strain measuring mode.

The invention claimed is:

1. A vinylsilane compound of the following Formula 1:

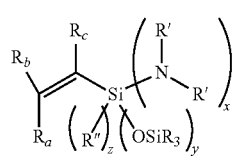

Formula 1 wherein R is independently selected from $C_1$-$C_{18}$ hydrocarbyl;
R" is selected from $C_1$-$C_6$ hydrocarbyl;
$R_a$, $R_b$ and $R_c$ are independently selected from hydrogen, methyl, ethyl and vinyl;

x and y are independently integers selected from 1 and 2;
z is an integer selected from 0 and 1; and x+y+z=3;

R' is independently selected from $C_1$-$C_{12}$ alkyl, $C_2$-$C_{12}$ alkenyl, $C_6$-$C_{18}$ aryl, $C_7$-$C_{18}$ alkylaryl, and tri($C_1$-$C_6$ alkyl, $C_6$-$C_{12}$ aryl or $C_7$-$C_{18}$ alkylaryl)silyl, wherein the two R' groups may be connected to form a ring and the ring may contain, further to the Si-bonded nitrogen atom, one or more of an oxygen atom, a nitrogen atom, an >N($C_1$-$C_6$ alkyl) group and a sulfur atom; and one R' may be —Si($CR_c$=$CR_aR_b$)($OSiR_3$)$_y$(R")$_z$, wherein $R_a$, $R_b$, $R_c$, R, R", y and z are independently as defined above and y+z=2.

2. The vinylsilane compound according to claim 1, which is represented by the following Formula 6:

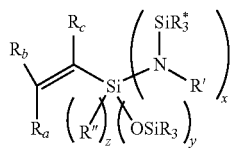

Formula 6 wherein R* is independently selected from $C_1$-$C_6$ alkyl, $C_6$-$C_{12}$ aryl and $C_7$-$C_{18}$ alkylaryl and the remaining parameters are as defined for Formula 1.

3. The vinylsilane compound according to claim 2, wherein R is (methyl, methyl, t-butyl); R' is selected from methyl, ethyl, n-propyl, n-butyl, pentyl, hexyl, heptyl and octyl; R* is selected from methyl and ethyl; R" is methyl; $R_a$, $R_b$ and $R_c$ are each hydrogen; and x=y=z=1.

4. The vinylsilane compound according to claim 1, wherein R is independently selected from $C_1$-$C_{18}$ alkyl, $C_2$-$C_{18}$ alkenyl, $C_2$-$C_{18}$ alkynyl, $C_6$-$C_{18}$ aryl and $C_7$-$C_{18}$ alkylaryl.

5. The vinylsilane compound according to claim 1, wherein R' is independently selected from methyl, ethyl, n-propyl, n-butyl, isobutyl, pentyl, hexyl and benzyl.

6. The vinylsilane compound according to claim 1, wherein the two R' groups are connected to form, together with the Si-bonded nitrogen atom, a 5- to 12-membered ring.

7. The vinylsilane compound according to claim 1, wherein R" is selected from $C_1$-$C_6$ alkyl and phenyl.

8. The vinylsilane compound according to claim 1, wherein $R_a$, $R_b$ and $R_c$ are identical.

9. The vinylsilane compound according to claim 1, wherein x, y and z are each 1.

10. The vinylsilane compound according to claim 1, wherein R is (methyl, methyl, t-butyl) or (phenyl, phenyl, phenyl) or (t-butyl, phenyl, phenyl) or (hexyl, hexyl, hexyl); R' is independently selected from methyl, ethyl, n-propyl, n-butyl, pentyl, hexyl, heptyl, octyl and benzyl (bonded via methyl group), or —NR'R' forms a morpholine group, pyrrolidine group, piperidine group or oxazolidine group; R" is methyl; $R_a$, $R_b$ and $R_c$ are each hydrogen; and x=y=z=1.

11. The vinylsilane compound according to claim 1, wherein R is (methyl, methyl, t-butyl) or (hexyl, hexyl, hexyl); R' is independently selected from methyl and ethyl, or —NR'R' forms a morpholine group, pyrrolidine group, piperidine group or oxazolidine group; R" is methyl; $R_a$, $R_b$ and $R_c$ are each hydrogen; and x=2, y=1 and z=0.

12. The vinylsilane compound according to claim 1, wherein R is (methyl, methyl, t-butyl) or (hexyl, hexyl, hexyl); R' is independently selected from methyl and ethyl, or —NR'R' forms a morpholine group, pyrrolidine group, piperidine group or oxazolidine group; R" is methyl; $R_a$ and $R_b$ are each hydrogen and $R_c$ is vinyl; and x=y=z=1.

13. A process for preparing the vinylsilane compound of Formula 1 as defined in claim 1, said process comprising reacting a dihalovinylsilane or trihalovinylsilane of the following Formula 2 with a tri($C_1$-$C_{18}$ hydrocarbyl)silanol of the following Formula 3 and a secondary aliphatic or aromatic amine of the following Formula 4 according to the following reaction scheme, in the presence of a proton scavenger:

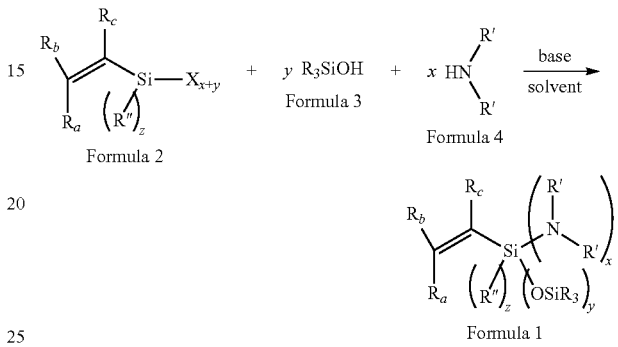

wherein R, R', R", $R_a$, $R_b$, $R_c$, x, y and z are as defined in claim 1 and X is halogen.

14. A process for preparing the vinylsilane compound of Formula 6 as defined in claim 2, said process comprising reacting a dihalovinylsilane or trihalovinylsilane of the following Formula 2 with a tri($C_1$-$C_{18}$ hydrocarbyl)silanol of the following Formula 3, a primary aliphatic or aromatic amine of the following Formula 4' and a halosilane of the following Formula 5 in the presence of a proton scavenger:

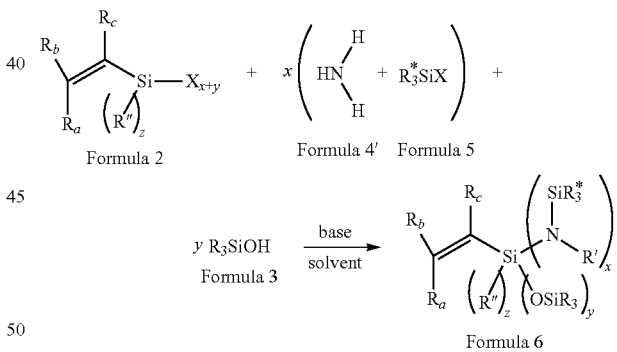

wherein R, R', R", R*, $R_a$, $R_b$, $R_c$, x, y and z are as defined in claim 2 and X is halogen.

15. A process for preparing an elastomeric polymer, said process comprising polymerizing at least one conjugated diene monomer, a vinylsilane compound as defined in claim 1 and-optionally one or more aromatic vinyl monomers in the presence of an initiator compound.

16. The process according to claim 15, wherein the polymerization is an anionic, radical or transition metal-catalyzed polymerization.

17. An elastomeric polymer obtainable by the process as defined in claim 15.

18. A non-cured polymer composition comprising the elastomeric polymer as defined in claim 17 and one or more further components selected from (i) components which are added to or formed as a result of the polymerization process used for making said polymer, (ii) components which remain after solvent removal from the polymerization process and (iii) components which are added to the polymer after completion of the polymer manufacturing process.

19. The polymer composition according to claim 18, comprising one or more components selected from extender oils, stabilizers and further polymers.

20. The polymer composition according to claim 18, further comprising one or more fillers.

21. The polymer composition according to claim 20, wherein the one or more fillers are selected from carbon black, carbon nanotubes, graphite, graphene, silica, carbon-silica dual-phase filler, clays, calcium carbonate, magnesium carbonate, lignin, glass particle-based fillers and starch-based fillers.

22. The polymer composition according to claim 18, further comprising one or more vulcanizing agents.

23. A vulcanized polymer composition obtainable by vulcanizing the polymer composition as defined in claim 22.

24. A method of making a vulcanized polymer composition, comprising the step of vulcanizing the polymer composition as defined in claim 22.

25. An article comprising at least one component formed from the vulcanized polymer composition as defined in claim 23.

26. The article according to claim 25, which is a tire, a tire tread, a tire side wall, a tire carcass, a belt, a gasket, a seal, a vibration damper, a footwear component, a golf ball or a hose.

* * * * *